US00PP34806P2

(12) United States Plant Patent
Hansen

(10) Patent No.: US PP34,806 P2
(45) Date of Patent: Dec. 6, 2022

(54) ***HOSTA* PLANT NAMED 'TERMS OF ENDEARMENT'**

(50) Latin Name: ***Hosta* hybrid**
Varietal Denomination: Terms of Endearment

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 67 days.

(21) Appl. No.: 17/300,990

(22) Filed: Jan. 10, 2022

(51) Int. Cl.
*A01H 6/12* (2018.01)
*A01H 5/02* (2018.01)

(52) U.S. Cl.
USPC ..... Plt./353

(58) Field of Classification Search
USPC ..... Plt./353
CPC ..... A01H 6/12; A01H 5/02
See application file for complete search history.

*Primary Examiner* — Keith O. Robinson

(57) ABSTRACT

A new and distinct *Hosta* plant named 'Terms of Endearment' of large, arching mounds of broadly ovate, bluish-green leaves having wide chartreuse margins upon emerging and maturing to creamy-yellow margins. The variegation is also attractively displayed with numerous featherings of intermediate colors between the center the leaf margins. The flowers are very pale purple to near white held just above the foliage beginning in late June for about four and a half weeks. 'Terms of Endearment' has excellent very large mounded habit and is useful in the landscape, as a specimen or en masse.

2 Drawing Sheets

Botanical classification: *Hosta* hybrid (Tratt.).
Variety denomination: 'Terms of Endearment'.

STATEMENT REGARDING PRIOR DISCLOSURES UNDER 37 CFR 1.77(b)(6)

*Hosta* 'Terms of Endearment' was first introduced by the inventor as a non-enabling description through the International Cultivar Registration Authority registration in early 2020. Other non-enabling disclosure include the website introduction by Walters Gardens, Inc. on Feb. 1, 2021 and the "Walters Gardens 2021-2022 Catalog" initially distributed on May 21, 2021. The first enabling disclosure in terms of a sale occurred on Aug. 2, 2021. No plants of *Hosta* 'Terms of Endearment' have been sold in this country or anywhere in the world, nor has any disclosure of the new plant been made, more than one year prior the filing date of this application.

BACKGROUND AND ORIGIN OF THE PLANT

The present invention relates to a new and distinct *Hosta* plant, *Hosta* 'Terms of Endearment' hereinafter also referred to as the new plant or by the cultivar name, 'Terms of Endearment'. *Hosta* 'Terms of Endearment' was hybridized by the inventor on Jun. 14, 2012 at a wholesale perennial nursery in Zeeland, Mich., USA. The female parent was a proprietary, unreleased sport known only as "streaked 'Elegans'" (not patented) and the male parent was 'Empress Wu' U.S. Plant Pat. No. 20,774. The new plant was assigned the breeder code 12-84-1 and passed the initial evaluation in the summer of 2014. It has been asexually propagated by division at the same nursery since 2018 and also by careful shoot tip plant tissue culture with the resultant asexually propagated plants having retained all the same traits as the original plant. *Hosta* 'Terms of Endearment' is stable and reproduces true to type in successive generations of asexual reproduction.

There are nearly 7,000 registered and established *Hosta* cultivars with The American *Hosta* Society, which is the International Cultivar Registration Authority for the genus *Hosta*. Several of these have green leaf blades with variegated margins. The most similar *Hosta* cultivars known to the applicant are 'Frances Williams' (not patented), 'Northern Exposure' (not patented), 'Earth Angel' (not patented), 'Band of Gold' (not patented) and 'Wu-La-La' U.S. Plant Pat. No. 31,309.

'Frances William' (a sport of 'Elegans') maintains a more yellowish variegated margins throughout the growing season, and the leaves are susceptible to burning appearing necrosis when mature. 'Northern Exposure' has more white variegated margin and 'Terms of Endearment' has a more yellowish variegated margin. 'Earth Angel' has leaves that are less bullate and more cordate in shape, the leaf margins are more creamy-yellow in maturity. 'Band of Gold' is more compact in habit, the leaf margins are lighter creamy-colored, and the flowers are higher above the foliage. 'Wu-La-La' has a more cordate leaf that is less bullate and less glaucous, the margin is not as broad and of a more chartreuse hue.

Other *Hosta* cultivars may have individual traits similar to 'Terms of Endearment' but the new plant differs from the above listed cultivars and all other *Hostas* known to the applicant, by the combination of the following traits.

1. Leaves are very large-sized, broadly ovate, with broadly acute apices and cordate base;
2. Arching leaves have a moderately-wavy chartreuse margin upon emerging and mature to a creamy-yellow;
3. Leaf center is bluish-green with numerous featherings of intermediate colors between the margin and center;

4. Flowers are pale purple to near white, densely arranged on scapes with the first flowers beginning to open just above the foliage;
5. Very large mounded habit and useful in the garden as edging or front border, in containers, as a specimen or en masse.

BRIEF DESCRIPTION OF THE DRAWING

The photograph of the new plant demonstrates the overall appearance of the plant, including the unique traits. The colors are as accurate as reasonably possible with color reproductions. Ambient light spectrum, temperature, source and direction may cause the appearance of minor variation in color.

The drawings show an eight-year-old 'Terms of Endearment' plant in a trial garden at a nursery in Zeeland, Mich. with supplement fertilizer and water as needed.

DETAILED BOTANICAL DESCRIPTION

Figure 1:
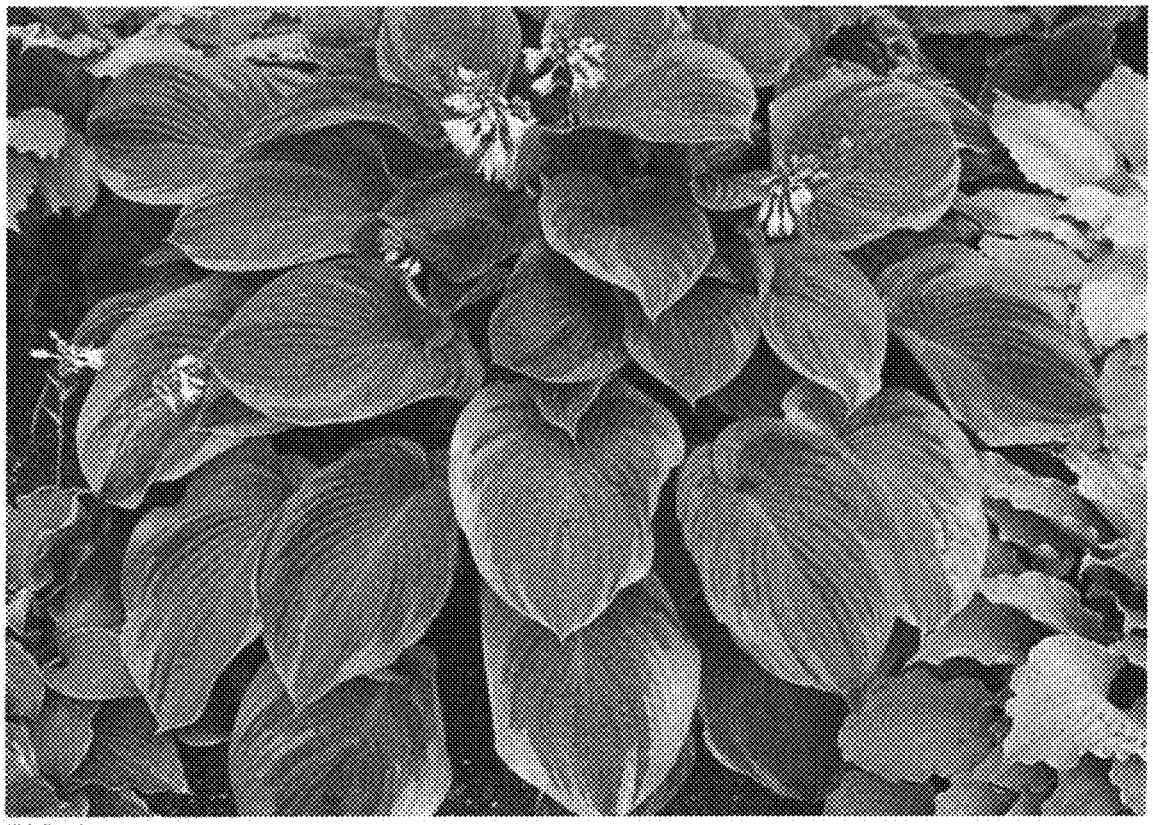
FIG. 1 shows the landscape foliage habit of a new plant at early flowering.
Figure 2:
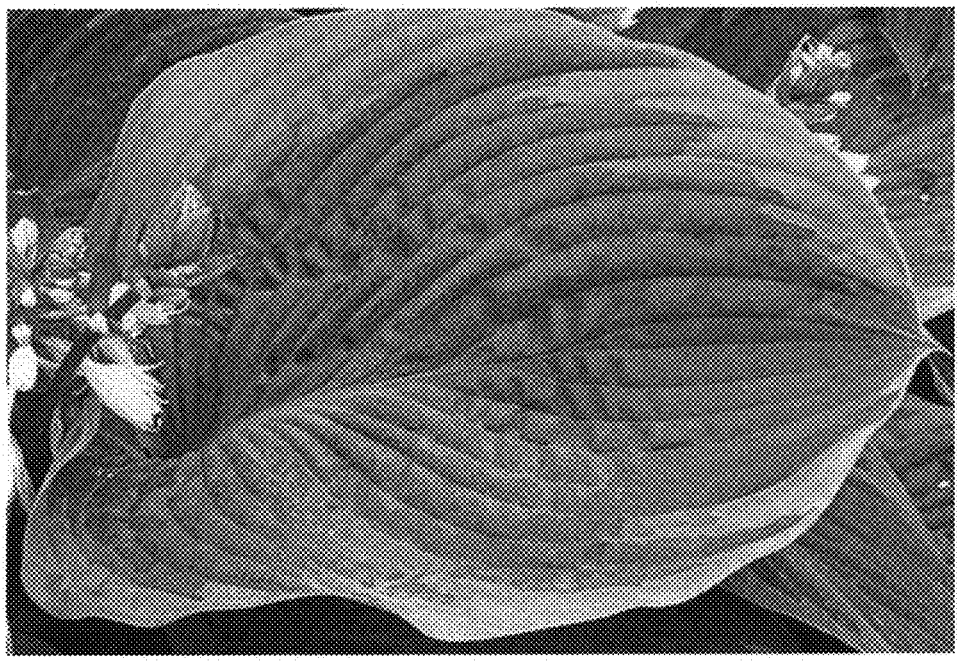
FIG. 2 shows a close-up of foliage.
Figure 3:
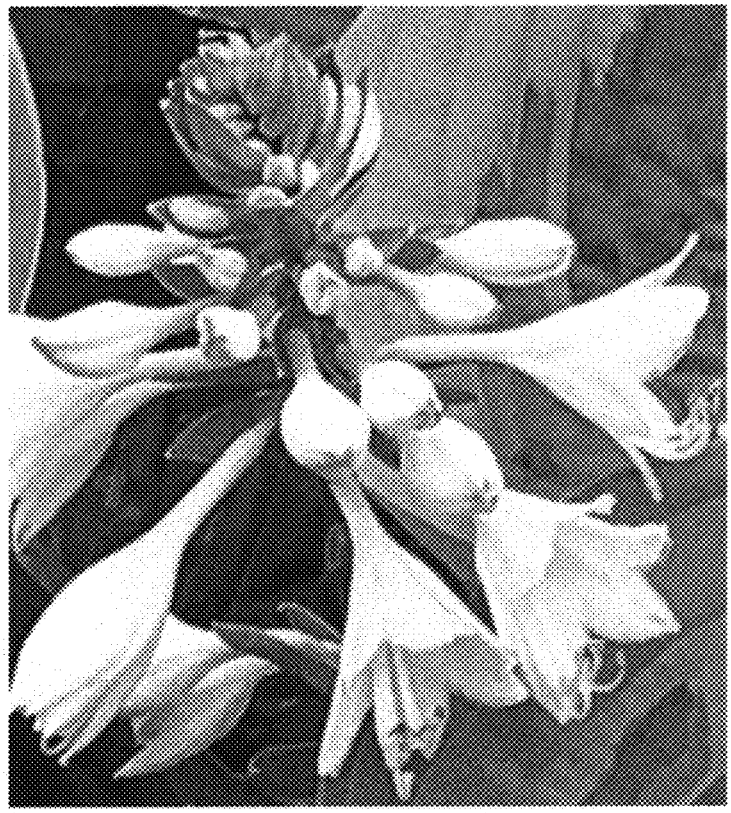
FIG. 3 shows a close-up of the flower scape with bracts flowers and buds.

The following descriptions and color references are based on the 2015 edition of The Royal Horticultural Society Colour Chart except where common dictionary terms are used. The new plant, *Hosta* 'Terms of Endearment', has not been observed under all possible environments. Those skilled in the art will appreciate that certain characteristics will vary with plants that are more mature or plants that are less mature. The phenotype may vary slightly with different environmental conditions, such as temperature, light, fertility, moisture and maturity levels, but without any change in the genotype. The following observations and size descriptions are of an eight-year-old plant in a shaded trial garden in Zeeland, Mich. with supplemental water and fertilizer.

Botanical classification: *Hosta* x hybrid;

Parentage: Female or seed parent the proprietary streaked sport of 'Elegans'; male or pollen parent 'Empress Wu';

Propagation: Garden division and sterile shoot tip plant tissue culture;

Time to initiate roots from tissue culture: About two to three weeks;

Growth rate: Moderately vigorous;

Crop time: About three months to four months to finish during the spring in a one-liter container from rooted tissue culture plantlet;

Rooting habit: Fleshy, lightly branching;

Root color: Nearest RHS NN155C when actively growing;

Plant shape and habit: Hardy herbaceous perennial with basal rosette of leaves emerging from rhizomes producing a large mound of arching petioles and leaves and erect scapes flowering above foliage;

Plant size: Foliage height to about 74 cm above soil line to the top of the leaves, to about 91 cm tall to the top of the flowers and to about 168 cm wide at the widest point slightly above soil line;

Foliage description: Broadly ovate; narrowly acute apex, cordate base; margin flat, entire; glabrous and lightly glaucous both surfaces; flexible but stiff; moderately bullate; moderately impressed adaxial veins and costate abaxial veins;

Leaf blade size: To about 36 cm long and about 28 cm wide about one-half of the way from the base; average about 34.5 cm long and 27 cm wide; margin width to about 2.5 cm wide, average 2.0 cm wide;

Leaf blade color: Early season and expanding adaxial margin nearest RHS 146D adaxial center nearest RHS 137A, adaxial intermediate colors comprising RHS 146D and RHS 145A; early season and expanding abaxial margin between RHS 146D and RHS 145A, abaxial center nearest RHS 137A, abaxial intermediate colors between RHA 147C and RHS 147B; mid-season and mature adaxial margins nearest RHS 11C, adaxial center between RHS NN137A and RHS 139A, adaxial intermediate colors comprising: RHS 191A, RHS 147C, RHS N144D, between RHS 194B and RHS 147C, between RHS 145C and RHS 146D, between RHS 145A and RHS N144D and between RHS 145D and RHS 145D; mid-season and mature abaxial margin nearest RHS 11C, abaxial center between RHS N138B and RHS N138C, abaxial intermediate colors comprising: RHS 146C, RHS 145A and RHS 191C;

Petiole: Glabrous and slightly glaucous both adaxial and abaxial; deeply concavo-convex proximally and more shallowly concavo-convex distally; stiff; to 40 cm long and 22 mm wide at base and about 15 mm deep near base, average about 38 cm long and 20 mm wide;

Petiole color: Adaxial margins about 1 mm wide nearest RHS 146C, center between RHS 138A and RHS 137D; abaxial margins about 1 mm wide nearest RHS 146C, between midrib and margin between RHS 145C and RHS 145D, midribs between RHS 145C and RHS 145D;

Veins: Fourteen to seventeen pairs and midrib; parallel; moderately impressed adaxial; costate and smooth abaxial;

Veins color: Young adaxial nearest RHS N144A, abaxial nearest RHS 145C; mature adaxial margin nearest RHS 11C, center between RHS 145B and RHS 145C, abaxial mature center nearest RHS 194B and margin nearest RHS 11C;

Flower description:

Buds one to two days prior to opening: Clavate with rounded apex and narrow tube base; about 44 mm long and 14 mm in diameter at the bulb with base narrowing in basal 20 mm to about 3 mm diameter;

Bud color: Nearest RHS NN155D with a blush of nearest RHS 84D distally and nearest RHS 145D proximally;

Flowers: Perfect; flared campanulate; outwardly; to 55 mm long to exserted stigma; corolla fused in basal 35 mm, free in the distal 14 mm, about 51 mm long and 40 mm wide at tepal apices, decreasing distally; corolla tube portion 20 mm long and 3.0 mm diameter; persists for a normal period, usually about one day on plant; mostly secund; flowers tightly arranged on scape;

Flowering period: Scapes remain effective with flowers beginning late-June for about four and a half weeks;

Flower number: About 46 flowers per scape;

Fragrance: No detectable fragrance;

Tepal: Two identical sets of three, glabrous; entire margins; about 51 mm long and 8 mm wide slightly above fusion point; fused in basal 35 mm; clavate with broadly acute apex; entire margin; base 20 mm fused into tube;

Tepal color: Adaxial nearest RHS NN155D with faint blush of nearest RHS 85D in center; adaxial between RHS NN155D and RHS 85D; corolla tube base adaxial nearest RHS NN155C and abaxial between RHS 145D and RHS NN155C;

Gynoecium: Single; 55 mm long; superior;

*Style*.—Cylindrical; about 41 mm long, 0.7 mm diameter; curved upward 90 degrees in distal 6.0 mm; color between RHS 145D and RHS NN155D distally and nearest RHS 145C proximally.

*Stigma*.—Puberulent; tri-lobed; about 1 mm across and 1 mm tall; color nearest RHS NN155A.

*Ovary*.—Ellipsoidal; superior; apex rounded; base rounded to truncate; smooth; to about 5 mm long and 2.5 mm diameter in middle; color nearest RHS 145A.

Androecium: Six;

*Filaments*.—Six, approximately 39 mm long and 0.3 mm in diameter; curved upward to about 90 degrees in the apical 6 mm; color distally nearest RHS NN155B, base between RHS NN155D and RHS 145D.

*Anthers*.—Ellipsoidal, with rounded ends; basifixed, longitudinally dehiscent; about 4 mm long and 1.5 mm wide; color nearest RHS 79A.

*Pollen*.—Spherical; less than 0.1 mm long; abundant; color nearest RHS 17B.

Peduncle: Cylindrical; usually one per mature division; about ten per plant; glabrous; glaucous; erect; to about 92 cm tall, and about 11 mm in diameter at base, average about 84 cm tall and 10 mm diameter at base;

Inflorescence: Flowering portion about 16 cm long and 14 cm wide; with large lavender blushed floral bracts subtending each flower; adaxial and abaxial color nearest RHS N138C with moderate to slight blush on abaxial side of nearest RHS 76B;

Peduncle color: Proximal portion below leaves nearest RHS 138C and distal portion nearest RHS 138A;

Pedicel: Cylindrical; glabrous; glaucous; about 11 mm long and 2 mm diameter; outwardly;

Pedicel color: Nearest RHS 148D;

Floral bracts: Each flower normally subtended by a single bract; ovate; acute apex and truncate base; entire margin; glabrous and glaucous abaxial and adaxial; to about 15 cm long 8 mm wide, decreasing distally;

Bract color: At time of flowering adaxial and abaxial between N138C and RHS 138C;

Fruit: Tri-valved dehiscent capsule; ellipsoidal to cylindrical with apex apiculate to acute and attenuate base; about 27 mm long and 7.0 mm diameter;

Fruit color: Nearest RHS 146B as maturing and RHS 161D when ripe;

Seed: Typically about 18 to 30 per capsule; endospermic; flattened-ellipsoidal wing surrounding embryo at one end of ellipse; to about 6 mm long, 3 mm wide and 1.5 mm thick at embryo;

Seed color: Nearest RHS 202A;

Disease resistance: The thick glaucous leaves provide some resistance to slug feeding and the new plant appears to show resistance to leaf necrosis found in many large-leafed variegated *Hosta*. Other resistance or susceptibility to pests (including: Odocoileus virginianus and Oryctotagus cuniculus) and diseases common to *Hostas* is equal that typical of other cultivars.

Plant growth: The new plant grows best and shows best coloration with plenty of moisture, adequate drainage and light shade, but is able to tolerate some drought when mature.

Hardiness: At least from USDA zone 3 through 8, and other disease resistance is typical of that of other *Hostas*.

It is claimed:

1. A new and distinct *Hosta* plant named 'Terms of Endearment' as herein described and illustrated.

* * * * *